US011041163B2

(12) United States Patent
Mammedov (10) Patent No.: US 11,041,163 B2
(45) Date of Patent: Jun. 22, 2021

(54) PRODUCTION OF IN VIVO N-DEGLYCOSYLATED RECOMBINANT PROTEINS BY CO-EXPRESSION WITH ENDO H

(71) Applicant: Tarlan Mammedov, Antalya (TR)

(72) Inventor: Tarlan Mammedov, Antalya (TR)

( * ) Notice: Subject to any disclaimer, the term of this patent is extended or adjusted under 35 U.S.C. 154(b) by 362 days.

(21) Appl. No.: 15/775,945

(22) PCT Filed: Nov. 13, 2015

(86) PCT No.: PCT/IB2015/058781
§ 371 (c)(1),
(2) Date: May 14, 2018

(87) PCT Pub. No.: WO2017/081520
PCT Pub. Date: May 18, 2017

(65) Prior Publication Data
US 2018/0327764 A1    Nov. 15, 2018

(51) Int. Cl.
C12N 15/82    (2006.01)
C12N 9/24    (2006.01)
C07K 14/32    (2006.01)
C07K 14/445    (2006.01)

(52) U.S. Cl.
CPC ....... *C12N 15/8242* (2013.01); *C12N 9/2402* (2013.01); *C07K 14/32* (2013.01); *C07K 14/445* (2013.01)

(58) Field of Classification Search
None
See application file for complete search history.

(56) References Cited

U.S. PATENT DOCUMENTS

| 8,545,909 | B2 | 10/2013 | Kappeler et al. | |
|---|---|---|---|---|
| 9,689,016 | B2 | 6/2017 | Marcel et al. | |
| 2004/0091957 | A1* | 5/2004 | Nock | C07K 16/065 435/68.1 |
| 2014/0186886 | A1* | 7/2014 | Mammedov | C07K 14/445 435/68.1 |
| 2015/0203814 | A1 | 7/2015 | Tseng et al. | |

FOREIGN PATENT DOCUMENTS

| RU | 2003130955 A | 4/2005 |
|---|---|---|
| WO | 2012170678 A1 | 12/2012 |
| WO | 2013119470 A1 | 8/2013 |
| WO | 2015080603 A1 | 6/2015 |
| WO | 2015095037 A1 | 6/2015 |

OTHER PUBLICATIONS

Geyer et al (Plant Biotechnology Journal, 2010, 8: 873-886).*
Gomord, Veronique, et al.; "Plant-Specific Glycosylation Patterns in the Context of Therapeutic Protein Production"; Plant Biotechnology Journal, vol. 8, Issue 5; May 9, 2010; pp. 564-587.
Faye, Loïc, et al., "Structure, Biosynthesis, and Function of Asparagine-Linked Glycans on Plant Glycoproteins"; Physiologia Plantarum, vol. 75, Issue 2; Feb. 1989; pp. 309-314.
Sparvoli, Francesca, et al.; "Misfolding and Aggregation of Vacuolar Glycoproteins in Plant Cells"; The Plant Journal, vol. 24, Issue 6; Dec. 2000; pp. 825-836.
D'Amico, Leone, et al.; "Bean Homologs of the Mammalian Glucose-Regulated Proteins: Induction by Tunicamycin and Interaction with Newly Synthesized Seed Storage Proteins in the Endoplasmic Reticulum"; The Plant Journal, vol. 2, Issue 4; Jul. 1992; pp. 443-455.

(Continued)

*Primary Examiner* — Stephen Uyeno
(74) *Attorney, Agent, or Firm* — Patshegen IP LLC; Moshe Pinchas (57) ABSTRACT

Plants have emerged as an alternative expression system and are increasingly being used byindustry and academia for producing target proteins. However, the ability of plants to glycosylate proteins can be a significant limitation for those proteins, which do not require N-glycosylation. For example, *Plasmodium falciparum* proteins, or A chain of human factor XIII do not carry N-linked glycans, or the protective antigen (PA) of *Bacillus* anthracisis not a glycoprotein; however, these proteins contain potential N-linked glycosylation sites that can be aberrantly glycosylated during expression in yeast, mammalian, or plant systems, potentially leading to reduced functionality and immunogenicity because of incorrect/altered folding and/or masking of epitopes. To overcome this problem we have recently developed a strategy of enzymatic deglycosylation of proteins in vivo by co-expressing with bacterial PNGase F (Peptide: N-glycosidase F) using transient expression in plants (WIPO Patent Application WO/2012/170678), which allowed production of malaria vaccine candidate Pfs48/45, which can provide a high transmission blocking (TB) activity (Mamedov et al., 2012). In addition, other deglycosylated antigens induced significantly higher levels of toxin-neutralizing antibody responses in mice than compared with glycosylated forms (Mamedov et al, manuscript has been submitted). Although a PNGase F treatment (in vivodeglycosylation) removes the oligosaccharide intact, but causes amino acid change in the deglycosylated protein due to deamidation of the asparagine (N) in the NxS/T site (sequence) into an aspartate (D). In this study, a strategy was developed for production of target proteins in plants in non-N-glycosylated form, but with no amino acid change in the NxS/T site of the resulting deglycosylated proteins, which can provide production of non-N-glycosylated recombinant proteins in plants or other eukaryotic system with a native-like fold. Thus, materials and methods for in vivo de-glycosylation of recombinant N-glycosylated proteins by co-expression with Endo-β-N-acetylglucosaminidase H (Endo H) in plants, using a transient expression system are described in this invention. A method of expressing active Endo Hin plants is also provided.

7 Claims, 5 Drawing Sheets
Specification includes a Sequence Listing.

(56) References Cited

OTHER PUBLICATIONS

Mammedov, Tarlan; Response to Written Opinion of the ISA for International Application No. PCT/IB2015/058781; dated Apr. 12, 2017; 12 pages.
Bennett, Lindsay D., et al.; "Implementation of Glycan Remodeling to Plant-Made Therapeutic Antibodies"; International Journal of Molecular Sciences, vol. 19, No. 2; Jan. 31, 2018; 17 pages.
Kruger, Julia; International Search Report for PCT/IB2015/058781 dated Jul. 26, 2016; 4 pages.
Kruger, Julia; Written Opinion of the International Searching Authority for PCT/IB2015/058781; dated Jul. 26, 2016; 7 pages.
Wang, Fei, et al.; "High-Level Expression of Endo-β-N-Acetylglucosaminidase H from Streptomyces plicatus in Pichia pastoris and its Application for the Deglycosylation of Glycoproteins"; PLoS ONE, vol. 10, No. 3; Mar. 17, 2015; 17 pages.
Mamedov, Tarlan, et al.; "Production of Non-Glycosylated Recombinant Proteins in Nicotiana benthamiana Plants by Co-Expressing Bacterial PNGase F"; Plant Biotechnology Journal, vol. 10; Feb. 2012; pp. 773-782.
Galen, James E., et al.; "Mucosal Immunization with Attenuated *Salmonella enterica* Serovar Typhi Expressing Protective Antigen of Anthrax Toxin (PA83) Primes Monkeys for Accelerated Serum Antibody Responses to Parenteral PA83 Vaccine"; The Journal of Infectious Diseases, vol. 199, No. 3; Dec. 19, 2008; pp. 326-335.
Milek, Richard L.B., et al.; "Plasmodium falciparum: Heterologous Synthesis of the Transmission-Blocking Vaccine Candidate Pfs48/45 in Recombinant Vaccinia Virus-Infected Cells"; Experimental Parasitology, vol. 90, No. 2; Oct. 1998; pp. 165-174.
Mamedov, Tarlan, et al.; "In Vivo Deglycosylation of Recombinant Proteins in Plants by Co-Expression with Bacterial PNGase F"; Bioengineered, 4:5; Jan. 17, 2013; pp. 338-342.

Mamedov, Tarlan, et al.; "Rational de novo Gene Synthesis by Rapid Polymerase Chain Assembly (PCA) and Expression of Endothelial Protein-C and Thromin Receptor Genes"; Journal of Biotechnology, 131:4; Aug. 10, 2007; pp. 379-387.
Tarentino, Anthony L., et al.; "Purification and Properties of an Endo-β-N-acetylglucosaminidase from Hen Oviduct"; The Journal of Biological Chemistry, vol. 251, No. 21; Nov. 10, 1976; pp. 6537-6543.
Trimble, Robert B., et al.; "Asparaginyl Glycopeptides with a Low Mannose Content Are Hydrolyzed by Endo-β-N-acetylglucosaminidase H*"; The Journal of Biological Chemistry, vol. 253, No. 13; Jul. 10, 1978; pp. 4508-4511.
Muramatsu, Takashi; "Demonstration of an Endo-glycosidase Acting on a Glycoprotein*" The Journal of Biological Chemistry, vol. 246, No. 17; Sep. 10, 1971; pp. 5535-5537.
Rouillard, Jean-Marie, et al.; "Gene2Oligo: Oligonucleotide Design for in vitro Gene Synthesis"; Nucleic Acids Research, vol. 32; Mar. 2004; pp. W176-W180.
Mamedov, Tarlan, et al.; In vivo Production of Non-Glycosylated Recombinant Proteins in Nicotiana benthamiana Plants by Co-Expression with Endo-β-N-acetylglucosaminidase H (Endo H) of Streptomyces plicatus'; PLoS ONE, vol. 12, No. 8; Aug. 21, 2017; 23 pages.
Office Action dated Aug. 28, 2019 of Japanese Patent Application No. 2018-54112 (English translation).
Office Action dated Aug. 5, 2019 of European Patent Application No. 15823378.3.
Office Action dated Jul. 26, 2019 of Russian Patent Application No. 2018117921.
Search Report dated Jul. 26, 2019 of Russian Patent Application No. 2018117921.
Mammedov, Tarlan et al.; "A Plant-Produced in vivo deglycosylated full-length Pfs48/45 as a Transmission-Blocking Vaccine Candidate against malaria"; Scientific Reports, Jul. 8, 2019; 12 pages.

* cited by examiner

ATGGGTTTCGTGCTGTTCAGCCAGCTGCCTTCTTTCCTTCTTGTGTCTACCCTTCTGC
TGTTCCTGGTGATCTCTCATTCTTGTAGGGCTCCAGCTCCTGCTCCTGTTAAGCAAG
GTCCTACTTCTGTGGCTTACGTTGAGGTGAACAACAACAGCATGCTGAACGTGGGA
AAGTACACCCTTGCTGATGGTGGTGGTAACGCTTTCGATGTGGCTGTGATTTTCGCT
GCTAACATCAACTACGATACCGGTACTAAGACCGCTTACCTGCACTTCAATGAGAAC
GTGCAGAGGGTGTTGGATAACGCTGTGACTCAGATTAGGCCTCTTCAGCAGCAGGG
TATTAAGGTGCTGCTTTCTGTGCTTGGTAACCACCAGGGTGCTGGTTTCGCTAATTTT
CCTAGTCAGCAGGCTGCTTCCGCTTTCGCTAAGCAACTTTCTGATGCTGTGGCTAAG
TACGGTCTGGATGGTGTGGATTTCGATGATGAGTACGGCTGAGTACGGTAACAACGGT
ACTGCTCAGCCTAACGATAGCTCTTTCGTGCATCTTGTGACCGCTCTGAGGGCTAAC
ATGCCTGATAAGATCATCAGCCTTTACAACATCGGTCCTGCTGCTTCCAGGCTTTCTT
ACGGTGGTGTTGATGTGAGCGATAAGTTCGATTACGCTTGGACCCTTACTACGGAA
CCTGGCAAGTTCCTGGTATTGCTTTGCCTAAGGCTCAGCTTTCTCCAGCTGCTGTTG
AGATTGGTAGGACCTCTAGGTCATACCGTGGCTGATCTTGCTAGAAGGACTGTGGATG
AGGGTTACGGTGTGTACCTTACCTACAACCTGGATGGTGGTGATAGGACCGCTGATG
TGTCTGCTTTCACCAGAGAGCTTTACGGTTCTGAGGCTGTGAGGACCCCTGATTAC
AAGGACGATGATGATAAGGATGAGCTGTAG (SEQ ID NO 1)

FIG. 2A

MGFVLFSQLPSFLLVSTLLLFLVISHSCRAPAPAPVKQGPTSVAYVEVNNNSMLNVGKY
TLADGGGNNAFDVAVIFAANINYDTGTKTAYLHFNENVQRVLDNAVTQIRPLQQQGIKV
LLSVLGNHQGAGFANFPSQQAASAFAKQLSDAVAKYGLDGVDFDDEYAEYGNNGTAQ
PNDSSFVHLVTALRANMPDKIISLYNIGPAASRLSYGGVDVSDKFDYAWNPYYGTWQV
PGIALPKAQLSPAAVEIGRTSRSTVADLARRTVDEGYGVYLTYNLDGGDRTADVSAFTR
ELYGSEAVRTPDYKDDDDKDEL (SEQ ID NO 2)

PRODUCTION OF IN VIVO N-DEGLYCOSYLATED RECOMBINANT PROTEINS BY CO-EXPRESSION WITH ENDO H

TECHNICAL FIELD

This document relates to materials and methods for producing recombinant proteins of interest in plants in a non-N-glycosylated form. A strategy was developed for production of target proteins in plants in non-N-glycosylated form, but with no amino acid change in the NxS/T site of the resulting deglycosylated proteins, which can provide production of non-N-glycosylated recombinant proteins in plants or other eukaryotic expression systems with a native-like fold. Materials and methods for in vivo de-glycosylation of recombinant N-glycosylated proteins by co-expression with Endo-β-N-acetylglucosaminidase H (Endo H) in plants, using a transient expression system are described. A method of expressing active Endo H in plants also is provided.

Replacement Sequence Listing entitled "Sequence_Listing.txt" (date of creation: May 9, 2018, size: 5.196 KB) is incorporated herein by reference.

SUMMARY OF THE INVENTION

Plants have emerged as an alternative expression system and are increasingly being used by industry and academia for producing target proteins. However, the ability of plants to glycosylate proteins can be a significant limitation for those proteins, which do not require N-glycosylation. For example, *Plasmodium falciparum* proteins, or A chain of human factor XIII do not carry N-linked glycans, or the protective antigen (PA) of *Bacillus anthracis* is not a glycoprotein; however, these proteins contain potential N-linked glycosylation sites that can be aberrantly glycosylated during expression in yeast, mammalian, or plant systems, potentially leading to reduced functionality and immunogenicity because of incorrect/altered folding and/or masking of epitopes. To overcome this problem we have recently developed a strategy of enzymatic deglycosylation of proteins in vivo by co-expressing with bacterial PNGase F (Peptide: N-glycosidase F) using transient expression in plants (WIPO Patent Application WO/2012/170678), which allowed production of malaria vaccine candidate Pfs48/45, which can provide a high transmission blocking (TB) activity (Mamedov et al., 2012). In addition, other deglycosylated antigens induced significantly higher levels of toxin-neutralizing antibody responses in mice than compared with glycosylated forms (Mamedov et al, manuscript has been submitted). Although a PNGase F treatment (in vivo deglycosylation) removes the oligosaccharide intact, but causes amino acid change in the deglycosylated protein due to deamidation of the asparagine (N) in the NxS/T site (sequence) into an aspartate (D). In this study, a strategy was developed for production of target proteins in plants in non-N-glycosylated form, but with no amino acid change in the NxS/T site of the resulting deglycosylated proteins, which can provide production of non-N-glycosylated recombinant proteins in plants or other eukaryotic system with a native-like fold. Thus, materials and methods for in vivo de-glycosylation of recombinant N-glycosylated proteins by co-expression with Endo-β-N-acetylglucosaminidase H (Endo H) in plants, using a transient expression system are described in this invention. A method of expressing active Endo H in plants is also provided.

BACKGROUND

N-glycosylation is a critical PTM for the correct folding and stability of many proteins, and the biological activity of many recombinant proteins produced in heterologous expression systems is dependent on their glycosylation status. However, some eukaryotic as well as bacterial proteins contain no N-glycans in the native host, but contain multiple potential N-glycosylation sites that can be aberrantly glycosylated when these proteins are expressed in heterologous eukaryotic expression systems, potentially leading to reduced functionality and immunogenicity due to incorrect/altered folding or masking of epitopes. For example, the Pfs48/45 protein of *Plasmodium falciparum* or A chain of human factor XIII do not carry N-linked glycans, and the protective antigen (PA) of *Bacillus anthracisis* not a glycoprotein; however, these proteins contain potential N-linked glycosylation sites that can be aberrantly glycosylated during expression in yeast, mammalian, or plant systems. Plants have emerged as an alternative expression system and are increasingly being used by industry and academia for producing target proteins. However, the ability of plants to glycosylate proteins also can be a significant limitation on the usefulness of plant-based expression systems. In our previous study, we have developed a strategy of enzymatic deglycosylation of proteins in vivo by co-expressing with bacterial PNGase F (Peptide: N-glycosidase F) using transient expression in plants (WIPO Patent Application WO/2012/170678). Using in vivo deglycosylation strategy, Pfs48/45 protein was produced in *N. benthamiana* in a non-N-glycosylated form and four mAbs, produced against different epitopes of Pfs48/45 protein, two of them conformation-specific, recognized the deglycosylated form of Pfs48/45 2- to 6-fold better than they recognized the glycosylated form of the same protein (Mamedov et al., 2012). In addition, the strongest binding to and the maximum mAb Ill signal inhibition were observed with in vivo PNGase F-deglycosylated Pfs48/45 only, while the in vitro deglycosylated, glycosylated (Mamedov et al., 2011) of Pfs48/45 were equivalent in their ability to inhibit the mAb Ill signal. In addition, this was tested also with other targets and results showed that only in vivo deglycoslated form had much more strong binding to antibodies, compared to in vitro deglycosylated and glycosylated forms, suggesting that aberrant glycosylation might have led to masking of important epitopes or caused incorrect/altered folding of the Pfs48/45 protein (Mamedov at al., 2012).

Endo-β-N-acetylglucosaminidase H (Endo H, EC3.2.1.96) is a glycohydrolase that is secreted by *Streptomyces plicatus* and a few other *Streptomyces* species (Tarentino et al., 1976). It cleaves the β-1, 4-glycosidic bond of the N-acetyl glucosamine core of oligosaccharides and leaves one N-acetylchitobiose attached to the asparagine residue of the glycoprotein (Trimble et al., 1978; Muramatsu 1971). The Endo H gene of *S. plicatus* is 939 bp (GenBank accession AAA26738.1) encodes a 28.9-kDa protein. Endo H from *Streptomyces plicatus* was recently expressed in *Pichia pastoris* and deglycosylated activity of *P. pastoris* produced Endo H was demonstrated in vitro, through both co-fermentation and post-fermentation treatments (Wang et al., 2015). However, N-deglycosylation of proteins in vivo condition by Endo H enzyme has not been achieved. In this study, in vivo de-glycosylation of recombinant N-glycosylated proteins by co-expression with Endo H in plants, using a transient expression system are described and presented.

OBJECT OF THE INVENTION

Figure 1A:
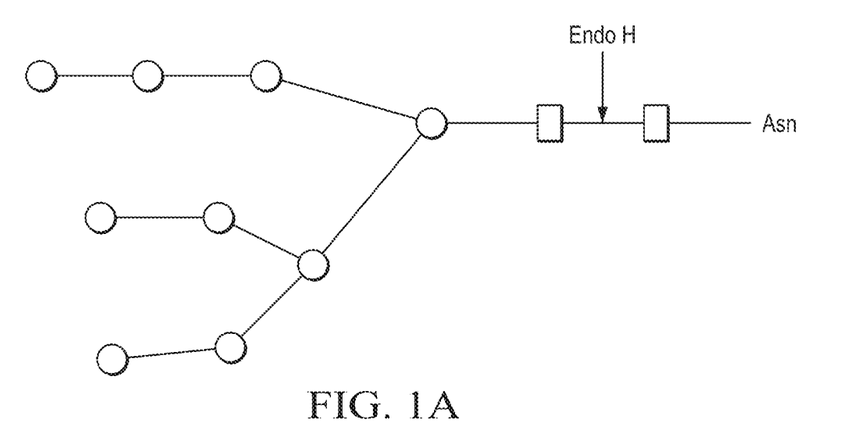
FIG. 1A shows Endo H cleaves between the two N-acetylglucosamine (GlcNAc) residues in the diacetylchitobiose core of the oligosaccharide, generating a truncated sugar molecule with one GlcNAc remaining on the asparagines (Asn).
Figure 1B:
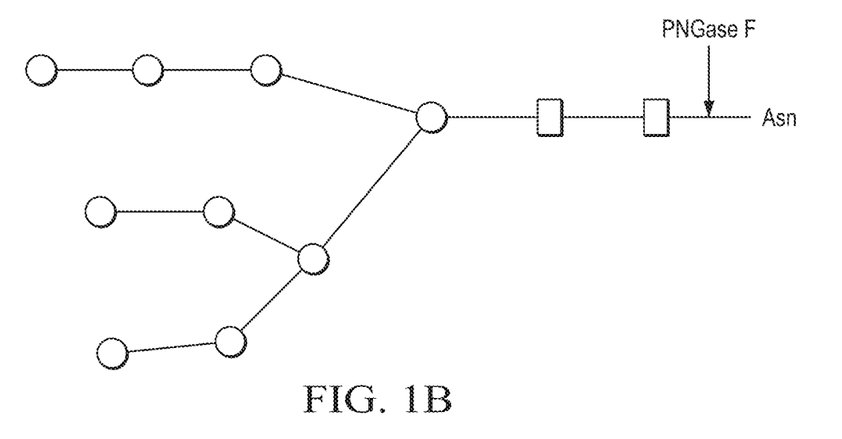
FIG. 1B shows Peptide-N-Glycosidase F (PNGase F), is an amidase that cleaves between the innermost GlcNAc and asparagine residues of high mannose, hybrid, and complex oligosaccharides from N-linked glycoproteins; □: N GlcNAc; ○: mannose.
Figure 2A:
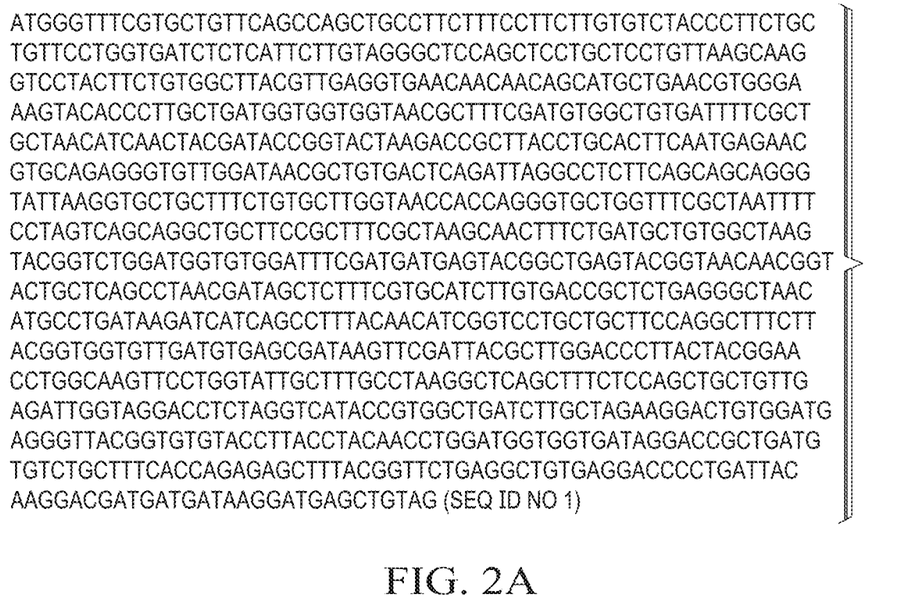
FIG. 2A shows bacterial Endo H gene nucleotide sequence, which was codon optimized using *N. benthamiana* codons.
Figure 2B:
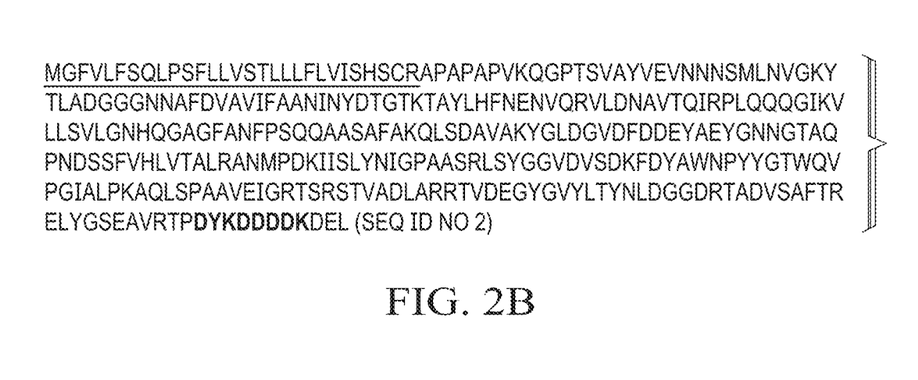
FIG. 2B shows amino acid sequence of Endo H expressed in *N. benthamiana* plant. PR-1a signal peptide sequence (MGFVLFSQLPSFLLVSTLLLFLVISHSCRA) (SEQ ID NO: 3) was added to the N-terminus is underlined. FLAG epitope (the affinity purification tag) followed by KDEL (SEQ ID NO: 5) (the ER retention signal) sequence (in bold) were added to the C-terminus.
Figure 3:
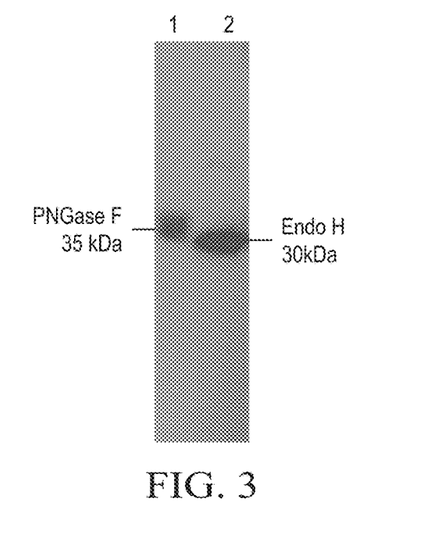

In our previous study, we have demonstrated deglycosylation of target protein in vivo by co expression target proteins with bacterial PNGase F (Mamedov T. WO/2012/170678, 2012; Mamedov et al., 2012). Although deglycosylation by PNGase F (in vivo or in vitro) removes the oligosaccharide intact, but causes amino acid change in the deglycosylated protein due to deamidation of the asparagine (N) in the NxS/T site (sequence) into an aspartate (D). At this point, other deglycosylating enzymes such as Endo-β-N-acetylglucosaminidase H (Endo H) that catalyze cleavage between two GlcNAc residues of the chitobiose core of N-linked glycans, leaving single GlcNAc residue attached to asparagines (FIG. 1), and opposite to PNGase F, deglycosylation by Endo H result in no change to the amino acid sequence in the NxS/T site of the resulting deglycosylated proteins. Since Endo H treatment produces no amino acid change in the resulting deglycosylated proteins, I hypothesized that deglycosylated proteins produced by Endo H may have more native-like folding, therefore better functional activity (immunogenicity, receptor binding, protein-antibody interaction, enzyme activity etc) compared with PNGase F deglycosylated form of the same protein. I also hypothesized that since Endo H cleavage leaving one GlcNAc residue attached to asparagines, the remaining monosacharide imparts a charge, thereby may increase the solubility and stability of deglycosylated proteins.

Industrial Application of the Invention

As described above, a PNGase F treatment (in vivo deglycosylation) removes the oligosaccharide intact, but causes amino acid change in the deglycosylated protein due to deamidation of the asparagine in the NxS/T site (sequence) into an aspartate. Endo H treatment results in no amino acid change in the NxS/T site of the resulting deglycosylated proteins. At this point it was hypothesized that deglycosylated proteins produced by Endo H may have more native-like folding, therefore better functional activity (immunogenicity, receptor binding, protein-antibody interaction, enzyme activity etc.) compared with PNGase F treated form of the same proteins. It was also hypothesized that since Endo H cleavage leaving one GlcNAc residue attached to asparagines, the remaining monosacharide imparts a charge, thereby may increase the solubility and stability of deglycosylated proteins. In this study, I demonstrate for the first time the expression of a deglycosylating bacterial enzyme Endo H in plants. I also demonstrate for the first time the deglycosylation of target proteins by Endo H in vivo in *N. benthamiana* plant. We demonstrate that the recombinant plant-produced Endo H is fully active in vivo and successfully cleaves N-linked glycans from PA83 and Pfs48/45 proteins. In addition, co-expression of PA83 with Endo H led to the accumulation of PA83 that was similar in size to that of the in vivo deglycosylated molecule by bacterial PNGase F. Importantly, results of our preliminary stability analyses demonstrate that Endo H in vivo deglycosylated PA83 appears to be more stable compared with glycosylated or PNGase F deglycosylated (in vivo) form of the same protein, especially at elevated temperature. In conclusion, all these results suggest that the Endo H co-expression strategy can be used to produce non-glycosylated recombinant proteins in the *N. benthamiana*-based transient expression system in native-like forms. In addition, the results of this study reveal the potential of Endo H deglycosylated PA83 as an anthrax and Pfs48/45 vaccine and support its further characterization for pre-clinical development. These results demonstrate that Endo H successfully cleaves N-linked glycans from all tested glycoproteins and suggest that the Endo H co-expression strategy can be used to produce non-glycosylated vaccine antigens, therapeutic proteins, antibodies and bacterial proteins (especially vaccine antigen candidates) enzymes.

In addition, this invention can be used for production of industrial enzymes, especially bacterial origin enzymes, in any eukaryotic system for increasing bioenergy/biofuel yield, as well as improving food quality, especially for producing native additives.

DESCRIPTION OF DRAWINGS

FIG. 2 shows the nucleotide and amino acid sequences of Endo H that were expressed in *N. benthamiana* as described herein.

FIG. 3 shows western blot analysis of Endo H in *N. benthamiana* plants. *N. benthamiana* plants, which were infiltrated with pGR-M-Endo H or pGR-M-PNGase F constructs, to produce Endo H and PNGase F. Leaf samples were taken at 5 dpi and were homogenized in three volumes of extraction buffer. After centrifugation at 13,000 g, samples were run on SDS-PAGE followed by Western blotting. Endo H and PNGase F were detected using polyclonal rabbit anti-flag tag (Cell signaling, cat no. 2368) antibody. Anti-rabbit IgG, HRP-linked antibody (Cell signaling, cat no. 7074) was used as a secondary antibody. 1-*N. benthamiana* plant expressing PNGase F (35 kDa); 2-*N. benthamiana* plant expressing Endo H (~30 kDa).

Figure 4A:
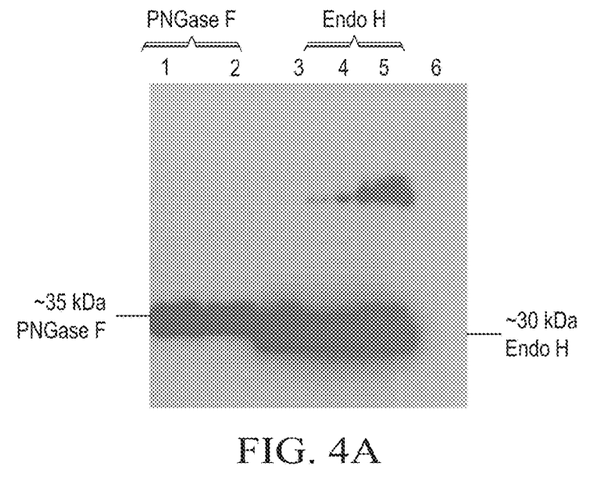
FIG. 4A shows that *benthamiana* plants leaves infiltrated with pGR-M-PNGase F/pGR-M-PA83 (1,2) or pGR-M-Endo H/pGR-M-PA83 (3-5), as indicated, were analyzed by western blot using polyclonal rabbit anti-flag tag (Cell signaling, cat no. 2368) antibody to detect PNGase F or Endo H. A: 6-non infiltrated *N. benthamiana* plant.
Figure 4B:
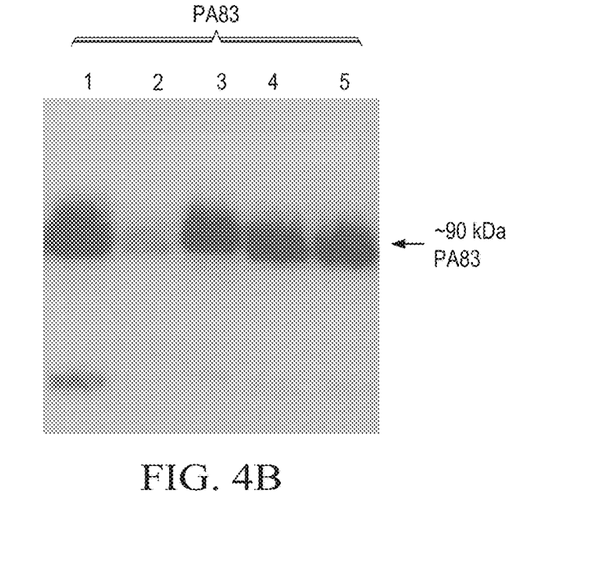
FIG. 4B shows western blot analysis of *N. benthamiana* plant infiltrated with pGR-M-PNGase F/pGR-M-PA83 (1,2) or pGR-M-Endo H/pGR-M-PA83 (3-5). To detect PA83 protein, anti-PA antibody (anti-*Bacillus anthracis* protective antigen antibody, BAP0101, cat. no. ab1988, Abcam) was used.

Endo H and PNGase F remained healthy at 7, 8 and 9 days post-infiltration (dpi) (FIG. 4) with no visible symptom development or change in growth when co-expression of target reached the highest level.

Figure 5:
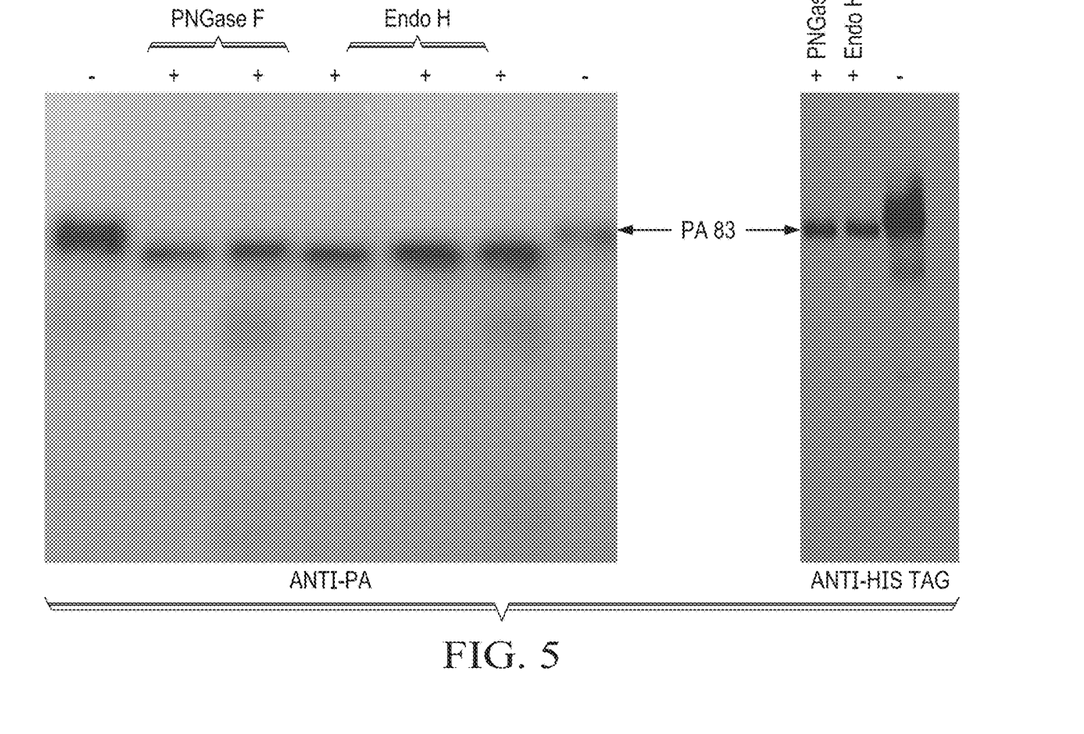
FIG. 5 depicts a western blot analysis of co-expression of *Bacillus anthracis* PA with bacterial PNGase F and Endo H as indicated in *N. benthamiana* plants. *N. benthamiana* plants were infiltrated with pGR-M-PNGase/pGR-M-PA83 or pGR-M-Endo H/pGR-M-PA83 constructs, for the pro- 
duction of deglycosylated PA83. Leaf samples were taken at 5 dpi and were homogenized in three volumes of extraction buffer. After centrifugation at 13
Figure 6:
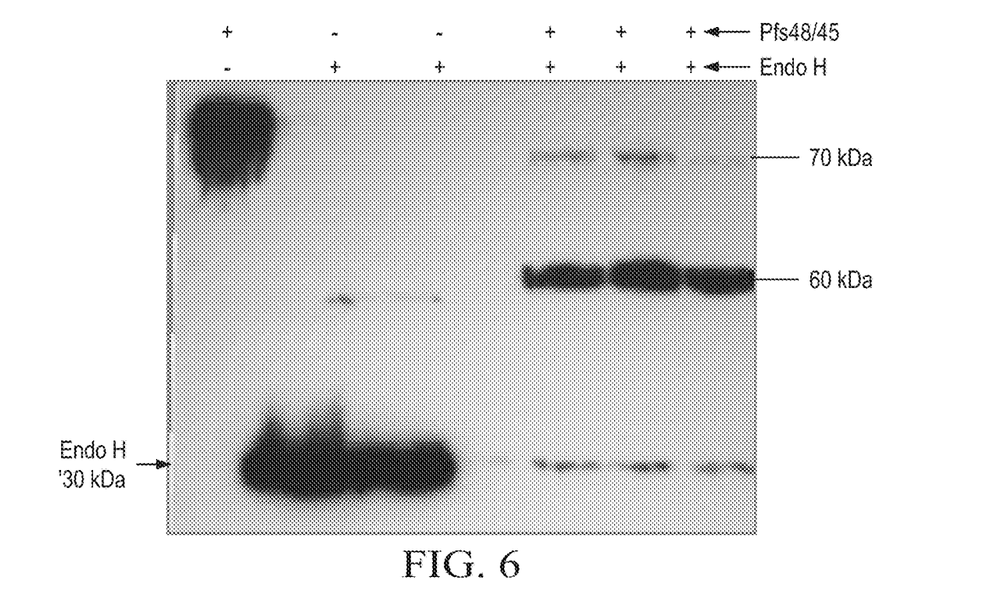
Figure 7A:
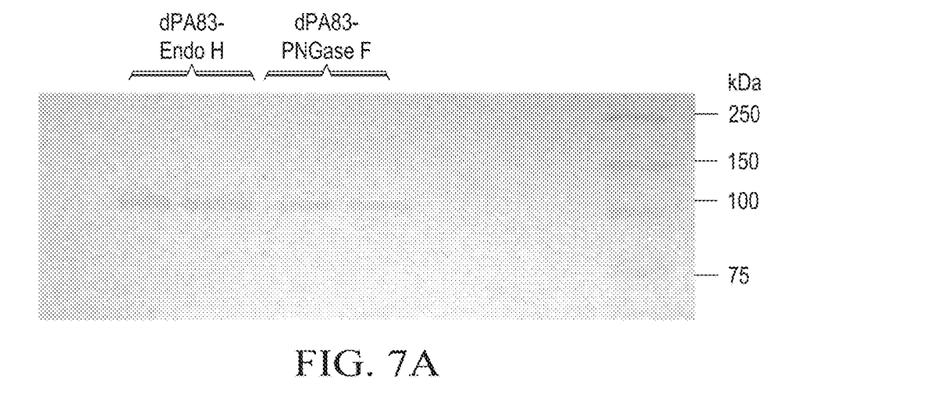
Figure 7B:
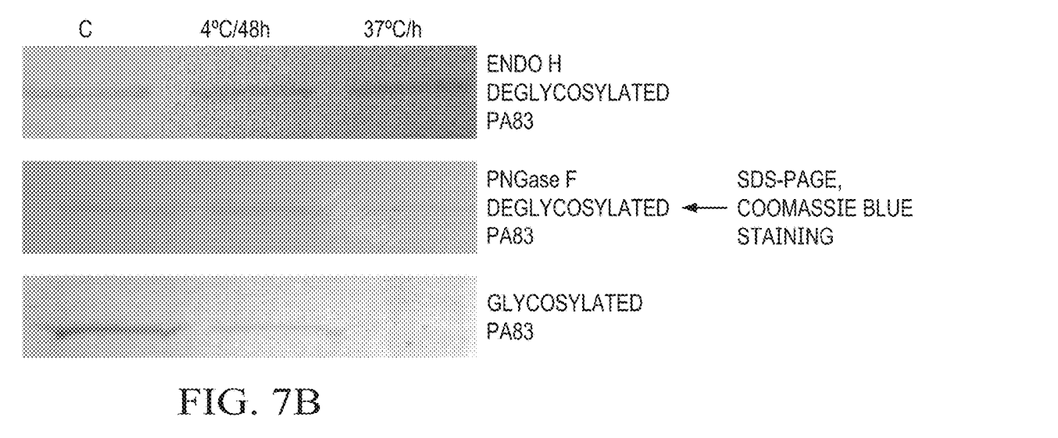
Figure 7C:
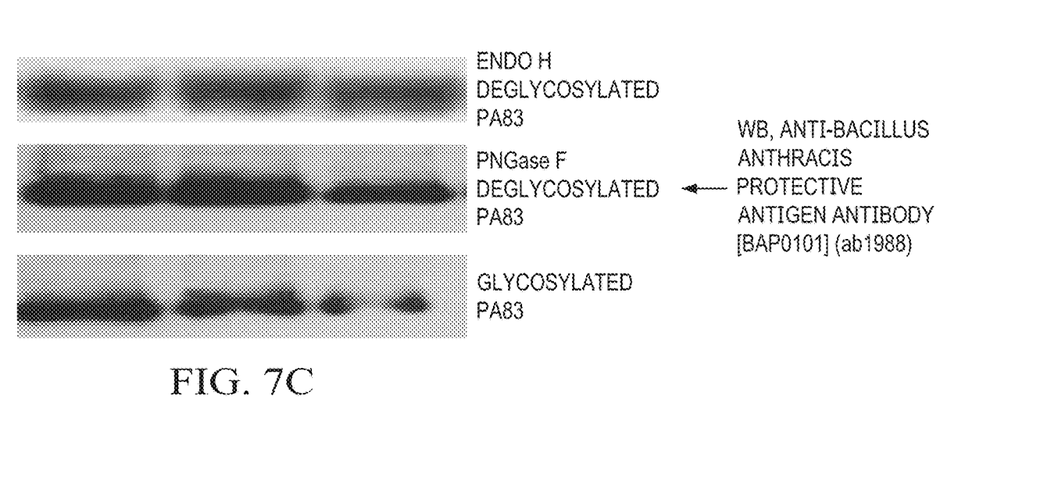

Example 3—De-Glycosylation Ability of Endo H; In Vivo Deglycosylation of Recombinant *B. anthracis* PA in *N. benthamiana* Plants by Co-Expressing Endo H To evaluate in vivo cleavage of N-linked oligosaccharides decorating PA83, Endo H and PA83 was transiently co-expressed in *N. benthamiana* plants via co-agroinfiltration. As a reference, bacterial PNGase F was also transiently co-expressed in *N. benthamiana* plants via co-agroinfiltration. It should be noted that PA of *B. anthracis* is not a glycoprotein, but it is glycosylated when expressed in *N. benthamiana* plants. The Western blot analysis performed at 5 dpi demonstrated a shift in the mobility of PA83 co-expressed with Endo H (FIG. 5), indicating protein deglycosylation. In addition, as shown by SDS-PAGE and the Western blot analysis, co-expression with Endo H led to the accumulation of PA83 that was similar in size to that of the in vivo deglycosylated molecule by bacterial PNGase F (Mamedov et al., 2012) suggesting that PA83 was enzymatically deglycosylated (FIG. 5).

Example 4—De-Glycosylation Ability of Endo H; In Vivo Deglycosylation of Pfs48/45 in *N. benthamiana* Plants by Co-Expressing Endo H Pfs48/45 is one of the leading candidates for transmission-blocking (TB) vaccine development. To evaluate in vivo cleavage of N-linked oligosaccharides decorating Pfs48/45, bacterial Endo H and Pfs48/45 protein of *Plasmodium falciparum* were transiently co-expressed in *N. benthamiana* plants via co-agroinfiltration with pGR-M-Pfs48/45 and pGR-M-Endo H constructs. As shown by SDS-PAGE and the Western blot analysis, co-expression with Endo H led to the accumulation of Pfs48/45 with molecular mass about ~60 kDa, which is similar in size to that of the in vitro deglycosylated molecule by PNGase F (see FIG. 4, Mamedov et al., 2012), indicating that Pfs48/45 was enzymatically deglycosylated (FIG. 5). These results, demonstrate that Endo H successfully cleaved N-linked glycans from PA83 and Pfs48/45 proteins and plant produced Endo H is enzymatically active in vivo, and suggest that the Endo H co-expression strategy can be used to produce therapeutic proteins in a non-glycosylated form in the *N. benthamiana*-based transient expression system.

Example 5—Purification of Deglycosylated PA83 Proteins Using HisPur™ Ni-NTA Resin and Preliminary Stability Analysis of Deglycosylated PA Protein Endo H and PNGase F co-expressed and deglycosylated forms of PA83 were purified using HisPur™ Ni-NTA Resin (ThermoFisher scientific, Cat. No. 8822). As shown by SDS-PAGE and Coomassie staining (FIG. 5A), the purified PA83 proteins were highly homogeneous. In addition, as shown by SDS-PAGE and (FIG. 5A) and the Western blot analysis, co-expression with Endo H led to the accumulation of PA83 that was similar in size to that of the in vivo deglycosylated molecule by bacterial PNGase F. To assess the affect of deglycosylation by Endo H and PNGase F on protein properties, deglycosylated forms of PA83 proteins were undergone a preliminary stability test of different forms of PA83, in the form 37° C. and 4° C. treatment and found that, Endo H in vivo deglycosylated PA83 appears to be slightly more stable compare with PNGase F glycosylated form, especially at elevated (37° C.) temperature.

Example 6—Binding of Anti-PA Monoclonal Antibody to Glycosylated, Endo H or PNGase F In Vivo Deglycosylated PA83 Variants Binding of anti-PA monoclonal antibody to glycosylated, Endo H or PNGase F in vivo deglycosylated PA83 variants were performed using IMAC purified PA83 antigens and *Bacillus anthracis* Protective Antigen Antibody (MA1-21675). Anti-PA antibody (anti-*Bacillus anthracis* protective antigen antibody, BAP0101, cat. no. ab1988, Abcam) showed similar binding to plant produced glycosylated and Endo H or PNGase F in vivo deglycosylated PA83 proteins (data not shown).

REFERENCES

IN VIVO DE-GLYCOSYLATION OF RECOMBINANT PROTEINS BY CO-EXPRESSION WITH PNGASE F. 12, 2012, WO/2012/170678.

Mamedov T, Ghosh A, Jones R M, Mett V, Farrance C E, Musiychuk K, et al. Production of non-glycosylated recombinant proteins in *Nicotiana benthamiana* plants by co-expressing bacterial PNGase F. Plant biotechnology journal. 2012; 10: 773-782.doi: 10.1111/j.1467-7652.2012.00694.x PMID: 22520228

Mamedov T, Yusibov V. In vivo deglycosylation of recombinant proteins in plants by co-expression with bacterial PNGase F. Bioengineered. 2013; 4: 338-342.

Mamedov, T. G., Padhye, N. V., Viljoen, H., Subramanian, A. 2007. "Rational de novo gene synthesis by rapid polymerase chain assembly (PCA) and expression of endothelial protein-C and thrombin receptor", Journal of Biotechnology, 131(4), 379-87.

Tarentino A L, Maley F. Purification and properties of an endo-β-N-acetylglucosaminidase from hen oviduct. Journal of Biological Chemistry. 1976; 251(21): 6537-6543. PMID: 977586

Trimble R B, Tarentino A L, Plummer T H, Maley F. Asparaginylglycopeptides with a low mannose content are hydrolyzed by endo-β-N-acetylglucosaminidase H. Journal of Biological Chemistry. 1978; 253(13): 4508-4511. PMID: 659430

Muramatsu T. Demonstration of an endo-glycosidase acting on a glycoprotein. Journal of Biological Chemistry. 1971; 246(17): 5535-5537. PMID: 4108054

Rouillard, J. M., Lee, W., Truan, G., Gao, X., Zhou, X., Gulari, E., 2004. Gene2Oligo: oligonucleotide design for in vitro gene synthesis. Nucleic Acids Res. 32, W176-W180.

Wang F, Wang X, Yu X, Fu L, Liu Y, Ma L, Zhai C. High-level expression of endo-β-N-acetylglucosaminidase H from *Streptomyces plicatus* in Pichiapastoris and its application for the deglycosylation of glycoproteins. PLoS One. 2015 Mar. 17; 10(3):e0120458. doi: 10.1371/journal.pone.0120458. eCollection 2015.

The invention claimed is:

1. A method of producing a deglycosylated polypeptide in a plant cell, the method comprising:

contacting a cytosol of the plant cell with a first nucleic acid comprising a first expression control sequence and a first expressible nucleic acid sequence operably linked to the first expression control sequence, the first expressible nucleic acid having the nucleic acid sequence of SEQ ID NO:1;

contacting the cytosol of the plant cell with a second nucleic acid comprising a second expression control sequence and a second expressible nucleic acid sequence operably linked to the second expression control sequence, the second expressible nucleic acid sequence encoding and an immunoactive polypeptide; and co-expressing the first nucleic acid and the second nucleic acid in the plant cell to generate the deglycosylated polypeptide, wherein the plant cell is a *Nicotiana benthamiana* cell.

2. The method of claim 1, wherein the polypeptide is immunoactive in humans.

3. The method of claim 1, wherein the second nucleic acid sequence encodes a peptide sequence that when produced in its native species is not glycosylated.

4. The method of claim 1, wherein the polypeptide is selected from Pfs48/45, PA83, and human factor XIII.

5. The method of claim 4, wherein the polypeptide is PA83, and wherein the polypeptide has increased stability compared to a glycosylated PA83 peptide.

6. The method of claim 4, wherein the polypeptide is PA83, and wherein the polypeptide has increased stability compared to a PNGase deglycosylated PA83 peptide.

7. The method of claim 1, wherein contacting the cytosol of the plant cell further comprises transforming the plant cell using *Agrobacterium*.

* * * * *

SEQUENCE LISTING

<160> NUMBER OF SEQ ID NOS: 5

<210> SEQ ID NO 1
<211> LENGTH: 942
<212> TYPE: DNA
<213> ORGANISM: Artificial Sequence
<220> FEATURE:
<223> OTHER INFORMATION: Synthetic: recombinant DNA

<400> SEQUENCE: 1

```
atgggtttcg tgctgttcag ccagctgcct tctttccttc ttgtgtctac ccttctgctg      60
ttcctggtga tctctcattc ttgtagggct ccagctcctg ctcctgttaa gcaaggtcct     120
acttctgtgg cttacgttga ggtgaacaac aacagcatgc tgaacgtggg aaagtacacc     180
cttgctgatg gtggtggtaa cgctttcgat gtggctgtga ttttcgctgc taacatcaac     240
tacgataccg gtactaagac cgcttacctg cacttcaatg agaacgtgca gagggtgttg     300
gataacgctg tgactcagat taggcctctt cagcagcagg gtattaaggt gctgctttct     360
gtgcttggta accaccaggg tgctggtttc gctaatttt ctagtcagca ggctgcttcc      420
gctttcgcta agcaactttc tgatgctgtg ctaagtacg tctggatgg tgtggatttc       480
gatgatgagt acgctgagta cggtaacaac ggtactgctc agcctaacga tagctctttc     540
gtgcatcttg tgaccgctct gagggctaac atgcctgata agatcatcag cctttacaac     600
atcggtcctg ctgcttccag gctttcttac ggtggtgttg atgtgagcga taagttcgat     660
tacgcttgga acccttacta cggaacctgg caagttcctg gtattgcttt gcctaaggct     720
cagctttctc cagctgctgt tgagattggt aggacctcta ggtctaccgt ggctgatctt     780
gctagaagga ctgtggatga gggttacggt gtgtaccta cctacaacct ggatggtggt     840
gataggaccg ctgatgtgtc tgctttcacc agagagcttt acggttctga ggctgtgagg    900
acccctgatt acaaggacga tgatgataag gatgagctgt ag                         942
```

<210> SEQ ID NO 2
<211> LENGTH: 313
<212> TYPE: PRT
<213> ORGANISM: Artificial Sequence
<220> FEATURE:
<223> OTHER INFORMATION: Synthetic: recombinant protein

<400> SEQUENCE: 2

```
Met Gly Phe Val Leu Phe Ser Gln Leu Pro Ser Phe Leu Leu Val Ser
1               5                   10                  15

Thr Leu Leu Phe Leu Val Ile Ser His Ser Cys Arg Ala Pro Ala
            20                  25                  30

Pro Ala Pro Val Lys Gln Gly Pro Thr Ser Val Ala Tyr Val Glu Val
        35                  40                  45

Asn Asn Asn Ser Met Leu Asn Val Gly Lys Tyr Thr Leu Ala Asp Gly
    50                  55                  60

Gly Gly Asn Ala Phe Asp Val Ala Val Ile Phe Ala Ala Asn Ile Asn
65                  70                  75                  80

Tyr Asp Thr Gly Thr Lys Thr Ala Tyr Leu His Phe Asn Glu Asn Val
                85                  90                  95

Gln Arg Val Leu Asp Asn Ala Val Thr Gln Ile Arg Pro Leu Gln Gln
            100                 105                 110

Gln Gly Ile Lys Val Leu Leu Ser Val Leu Gly Asn His Gln Gly Ala
        115                 120                 125

Gly Phe Ala Asn Phe Pro Ser Gln Gln Ala Ala Ser Ala Phe Ala Lys
```

```
            130                 135                 140
Gln Leu Ser Asp Ala Val Ala Lys Tyr Gly Leu Asp Gly Val Asp Phe
145                 150                 155                 160

Asp Asp Glu Tyr Ala Glu Tyr Gly Asn Asn Gly Thr Ala Gln Pro Asn
                165                 170                 175

Asp Ser Ser Phe Val His Leu Val Thr Ala Leu Arg Ala Asn Met Pro
            180                 185                 190

Asp Lys Ile Ile Ser Leu Tyr Asn Ile Gly Pro Ala Ala Ser Arg Leu
        195                 200                 205

Ser Tyr Gly Gly Val Asp Val Ser Asp Lys Phe Asp Tyr Ala Trp Asn
    210                 215                 220

Pro Tyr Tyr Gly Thr Trp Gln Val Pro Gly Ile Ala Leu Pro Lys Ala
225                 230                 235                 240

Gln Leu Ser Pro Ala Ala Val Glu Ile Gly Arg Thr Ser Arg Ser Thr
                245                 250                 255

Val Ala Asp Leu Ala Arg Arg Thr Val Asp Glu Gly Tyr Gly Val Tyr
            260                 265                 270

Leu Thr Tyr Asn Leu Asp Gly Gly Asp Arg Thr Ala Asp Val Ser Ala
        275                 280                 285

Phe Thr Arg Glu Leu Tyr Gly Ser Glu Ala Val Arg Thr Pro Asp Tyr
    290                 295                 300

Lys Asp Asp Asp Asp Lys Asp Glu Leu
305                 310
```

<210> SEQ ID NO 3
<211> LENGTH: 30
<212> TYPE: PRT
<213> ORGANISM: Nicotiana benthamiana
<220> FEATURE:
<221> NAME/KEY: misc_feature
<223> OTHER INFORMATION: recombinant protein

<400> SEQUENCE: 3

```
Met Gly Phe Val Leu Phe Ser Gln Leu Pro Ser Phe Leu Leu Val Ser
1               5                   10                  15

Thr Leu Leu Leu Phe Leu Val Ile Ser His Ser Cys Arg Ala
            20                  25                  30
```

<210> SEQ ID NO 4
<211> LENGTH: 8
<212> TYPE: PRT
<213> ORGANISM: Artificial Sequence
<220> FEATURE:
<223> OTHER INFORMATION: Synthetic: FLAG sequence

<400> SEQUENCE: 4

```
Asp Tyr Lys Asp Asp Asp Asp Lys
1               5
```

<210> SEQ ID NO 5
<211> LENGTH: 4
<212> TYPE: PRT
<213> ORGANISM: Artificial Sequence
<220> FEATURE:
<223> OTHER INFORMATION: Synthetic sequence

<400> SEQUENCE: 5

```
Lys Asp Glu Leu
1
```